United States Patent
Roduit et al.

[11] Patent Number: 6,103,906
[45] Date of Patent: Aug. 15, 2000

[54] PROCESS FOR THE PREPARATION OF 2,6-PYRIDINEDICARBOXYLIC ACID ESTERS

[75] Inventors: Jean-Paul Roduit, Grône; Yves Bessard, Sierre, both of Switzerland

[73] Assignee: Lonza, Ltd., Gampel/Valasis, Switzerland

[21] Appl. No.: 09/038,977

[22] Filed: Mar. 12, 1998

[30] Foreign Application Priority Data

Mar. 12, 1997 [CH] Switzerland .............. 0595/97

[51] Int. Cl.[7] ................................ C07D 213/30
[52] U.S. Cl. ............................................... 546/327
[58] Field of Search ............................. 546/327

[56] References Cited

U.S. PATENT DOCUMENTS

| | | | |
|---|---|---|---|
| 4,995,902 | 2/1991 | Brummer | 546/315 |
| 5,142,057 | 8/1992 | Suto et al. | 546/316 |
| 5,925,765 | 7/1999 | Bessard et al. | 546/327 |

FOREIGN PATENT DOCUMENTS

| | | |
|---|---|---|
| 872394 | 3/1979 | Belgium . |
| 820986 | 7/1996 | European Pat. Off. . |
| 1620174 | 4/1982 | Germany . |
| 7-126176 | 5/1995 | Japan . |
| 568462 | 7/1975 | U.S.S.R. . |
| 2009163 | 6/1979 | United Kingdom . |
| WO 93/18005 | 9/1996 | WIPO . |

OTHER PUBLICATIONS

Kudo Catalyst, vol. 36, No. 8, pp. 580–584, Recent Topics in Complex Catalyst Reaction, pp. 1–16, 1994.
Jour. of Molecular Catalysis, 66, pp. 277–288, 1991.
Iovel, I., et al., Synth. Commun., vol. 22, No. 18, (1992), pp. 2691–2696.
Wang, G., et al., Synlett, No. 5, (1992), pp. 422 to 424.

Primary Examiner—Jane Fan
Attorney, Agent, or Firm—Fisher, Christen & Sabol

[57] ABSTRACT

A process for the preparation of 2,6-pyridinedicarboxylic acid esters of the general formula:

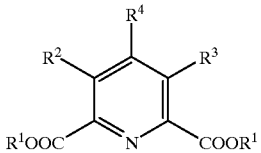

I wherein $R^1$ is a $C_1$–$C_6$-alkyl group, a $C_3$–$C_6$-cycloalkyl group, an aryl group or an arylalkyl group, and $R^2$ and $R^3$ independently of one another are hydrogen or chlorine and $R^4$ is hydrogen, a $C_1$–$C_6$-alkyl group, a $C_1$–$C_6$-alkoxy group or fluorine. The 2,6-pyridinedicarboxylic acid esters are obtained by reaction of the corresponding halopyridines with carbon monoxide and an alcohol of the general formula:

$$R^1\text{—OH} \qquad \qquad III$$

wherein $R^1$ has the abovementioned meaning, in the presence of a base and of a complex of palladium with a bis-diphenylphosphine. 2,6-Pyridinedicarboxylic acid esters are intermediates for the preparation of compounds having anti-inflammatory action.

14 Claims, No Drawings

PROCESS FOR THE PREPARATION OF 2,6-PYRIDINEDICARBOXYLIC ACID ESTERS

BACKGROUND OF THE INVENTION

1. Field of the Invention

The present invention relates to a process for the preparation of 2,6-pyridinedicarboxylic acid esters by reaction of halogenated pyridines with carbon monoxide and an alcohol in the presence of a base and a catalyst. 2,6-Pyridinedicarboxylic acid esters are important intermediates, e.g., for the preparation of compounds having anti-inflammatory action (Japanese Published Patent Application (Kokai) No. 93/143799). The 2,6-pyridinedicarboxylic acid esters which can be prepared according to the invention have the general formula:

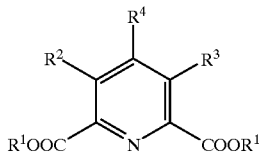

I wherein $R^1$ is a $C_{12}$–$C_6$-alkyl group, a $C_3$–$C_6$-cycloalkyl group, an aryl group or an arylalkyl group, and $R^2$ and $R^3$ independently of one another are hydrogen or chlorine and $R^4$ is hydrogen, a $C_1$–$C_6$-alkyl group, a $C_1$–$C_6$-alkoxy group or fluorine.

2. Background Art

Known processes for the preparation of 2,6-pyridinedicarboxylic acid esters are based on the direct chemical oxidation of 2,6-dimethylpyridine (I. Iovel, M. Shymanska, Synth. Commun., (1992), 22, 2691; G. Wang, D. E. Bergstrom, Synlett (1992), 422; Belgian Patent No. 872,394; Soviet Patent No. 568,642). Although high yields are in some cases achieved here, the processes are associated with disadvantages because of the use of expensive and/or toxic reagents. A process for the preparation of 2,6-pyridinedicarboxylic acid esters by carbonylation of 2,6-dichloropyridine using a nickel catalyst is known [International Published Patent Application No. (WO) 93/18005]. A disadvantage of this process is that the reaction is carried out at high pressure, the 2,6-pyridinedicarboxylic acid esters are only obtained in moderate yields and a high proportion of monocarbonylated side product is formed.

BROAD DESCRIPTION OF THE INVENTION

An object of the invention was to make available an economical process with which, starting from halopyridines, 2,6-pyridinedicarboxylic acid esters of the general formula I can be prepared in high yields. Other objects and advantages of the invention are set out herein or are obvious herefrom to one skilled in the art.

In the process of the invention, halopyridines of the general formula:

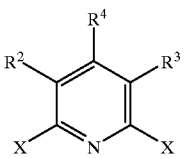

II wherein $R^2$, $R^3$, and $R^4$ have the above-mentioned meanings and X is chlorine or bromine, are reacted with carbon monoxide and an alcohol of the general formula:

$R^1$—OH            III wherein $R^1$ has the above-mentioned meaning, in the presence of a base and of a complex of palladium, using a bisdiphenylphosphine of the general formula:

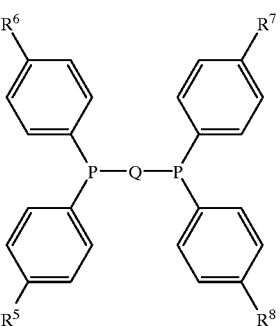

IV wherein Q is a $C_3$–$C_8$-alkanediyl group or a 1,1'-ferrocenediyl group having cyclopentadienyl groups which are optionally substituted by $C_1$–$C_4$-alkyl or aryl groups and $R^5$ to $R^8$ independently of one another are hydrogen, $C_1$–$C_4$-alkyl, $C_1$–$C_4$-alkoxy, monofluoromethyl, difluoromethyl, trifluoromethyl, fluorine, aryl, aryloxy, cyano or dialkylamino.

$R^1$ is a straight-chain or branched alkyl group having 1 to 6 C atoms, a cyloalkyl group having 3 to 6 C atoms, an aryl group or an arylalkyl group.

Especial mention may be made of methyl, ethyl, propyl, isopropyl, butyl, isobutyl, tert-butyl, pentyl and its isomers and also hexyl and its isomers, cyclopropyl, cyclobutyl, cyclopentyl, and also cyclohexyl. Aryl groups here are in particular to be understood as being monocyclic or polycyclic systems, such as, phenyl, naphthyl, biphenyl or anthracenyl. These can carry one or more identical or different substituents, for example, lower alkyl groups such as methyl, halogenated alkyl groups such as trifluoromethyl, lower alkoxy groups such as methoxy, or lower alkylthio (alkanesulfanyl) or alkanesulfonyl groups such as methylthio or ethanesulfonyl. Substituted phenyl here and in the following is in particular to be understood as being groups such as fluorophenyl, methoxyphenyl, tolyl or trifluoromethylphenyl, with the substituents preferably being in the para-position.

Accordingly, arylalkyl is to be understood as being the groups formed from lower alkyl groups, in particular $C_1$–$C_6$-alkyl, by replacement of a hydrogen atom by one of the aryl groups defined above, for example, benzyl or phenylethyl.

$R^1$ particularly preferably is methyl, ethyl, butyl or cyclohexyl.

$R^2$ and $R^3$ independently of one another are hydrogen or chlorine.

$R^2$ and $R^3$ are particularly preferably hydrogen.

$R^4$ is hydrogen, a straight-chain or branched alkyl group having 1 to 6 C atoms or a straight-chain or branched alkoxy group having 1 to 6 C atoms or fluorine. Especial mention is made of methyl, ethyl, propyl, isopropyl, butyl, isobutyl, tert-butyl, pentyl and its isomers and also hexyl and its isomers, methoxy, ethoxy, propoxy, isopropoxy, butoxy, isobutoxy, tert-butoxy, pentoxy and its isomers, and also hexoxy and its isomers. Particularly preferably $R^4$ has the meaning hydrogen.

X is chlorine or bromine; particularly X is chlorine.

Halopyridines of the general formula 11 are commercially available.

Preferably, methyl, ethyl, butyl or cyclohexyl esters ($R^1$= methyl, ethyl, butyl, cyclohexyl) are prepared by the process according to the invention by employing methanol, ethanol, butanol or cyclohexanol, respectively, as alcohol (111).

The reaction is carried out in the presence of a base. Highly suitable bases are, for example, alkali metal and alkaline earth metal acetates, carbonates, hydrogencarbonates, phosphates or hydrogenphosphates. Especial mention is made of sodium acetate, potassium acetate, magnesium acetate, calcium acetate, sodium carbonate, potassium carbonate, magnesium carbonate, calcium carbonate, sodium hydrogencarbonate, potassium hydrogencarbonate, magnesium phosphate, calcium phosphate, sodium dihydrogenphosphate, potassium dihydrogenphosphate, disodium hydrogenphosphate, dipotassium hydrogenphosphate, magnesium hydrogenphosphate and calcium hydrogenphosphate. Sodium acetate is particularly suitable.

The catalytically active palladium bisdiphenyl phosphine complex is advantageously formed in situ, by reacting a Pd(II) salt (e.g., the chloride or the acetate) or a suitable Pd(II) complex [e.g., bis(triphenylphosphine) palladium(II) chloride] with the diphosphine. The Pd(II) salt or Pd(II) complex preferably employed is palladium(II) acetate or bis(triphenylphosphine) palladium(II) chloride. The palladium is preferably employed in an amount from 0.05 to 0.4 mol percent of Pd(II), based on the halogen compound (II). The diphosphine is advantageously employed in excess (based on Pd), preferably in an amount form 0.2 to 5 mol percent, likewise based on the halogen compound (II).

Bisdiphenylphosphines (IV) advantageously employed are those in which Q is a straight-chain or branched alkanediyl group having 3 to 6 C atoms. Especial mention is made of propane-1,3-diyl, propane-1,2-diyl, butane-1,4-diyl, butane-1,3-diyl, butane-1,2-diyl, pentanediyl and its isomers and also hexanediyl and its isomers. Those are preferably employed in which Q is a straight-chain alkanediyl group having 3 to 6 C atoms. Especial mention is made of propane-1,3-diyl, butane-1,4-diyl, pentane-1,5-diyl and also hexane-1,6-diyl. 1,4-Bis(diphenylphosphino) butane is particularly preferred.

Bis-diphenylphosphines (IV) are likewise advantageously employed in which Q is a 1,1'-ferrocenediyl group having cyclopentadienyl groups which are optionally substituted by $C_1$–$C_4$-alkyl or aryl groups. $C_1$–$C_4$-alkyl substituents employed are preferably methyl, ethyl, propyl, isopropyl, butyl, isobutyl and tert-butyl; and methyl and ethyl are particularly preferred. Aryl substituents employed here are preferably phenyl or optionally substituted phenyl. 1,1'-Bis (diphenylphosphino)ferrocene is particularly preferably employed.

$R^5$ to $R^8$ are, independently of one another, hydrogen, $C_1$–$C_4$-alkyl, $C_1$–$C_4$-alkoxy, monofluoromethyl, difluoromethyl, trifluoromethyl, fluorine, aryl, aryloxy, cyano or dialkylamino.

$C_1$–$C_4$-alkyl substituents employed are advantageously methyl, ethyl, propyl, isopropyl, butyl, isobutyl and tert-butyl; and methyl and ethyl are particularly preferred. $C_1$–$C_4$-alkoxy substituents employed are advantageously methoxy, ethoxy, propoxy, isopropoxy, butoxy, isobutoxy and tert-butoxy; and methoxy and ethoxy are particularly preferred. Aryl substituents employed here are advantageously phenyl or optionally substituted phenyl. Aryloxy substituents employed are advantageously phenoxy and optionally substituted phenoxy. Substituted phenoxy is understood as being, in particular, groups such as fluorophenoxy, methoxyphenoxy, tolyloxy or trifluoromethylphenoxy, the substituents preferably being in the para-position. Dialkylamino substituents employed are preferably amines having $C_1$–$C_2$-alkyl radicals. Especial mention is made of dimethylamino and diethylamino.

The alcohol (III) can also serve as a solvent. If desired, an additional solvent can be employed. An additional solvent is either a non-polar organic solvent, such as, toluene or xylene, or a polar organic solvent, such as, acetonitrile, tetrahydrofuran or N, N-dimethylacetamide.

The reaction is advantageously carried out at a reaction temperature of 100° to 250° C., preferably at 1400 to 195° C. and a carbon monoxide pressure of advantageously 1 to 200 bar, preferably 5 to 50 bar. After a reaction time of, customarily, 1 to 20 hours, the compound of the general formula I is obtained in high yield.

The following examples illustrate the procedure of the process according to the invention.

EXAMPLE 1

Dimethyl 2,6-pyridinedicarboxylate 1.48 g (10 mmol) of 2,6-dichloropyridine, 166 mg of 1,1'-bis(diphenylphosphino)ferrocene (3 mol percent based on the 2,6-dichloropyridine), 46 mg of palladium(II) acetate (0.2 mol percent based on the 2,6-dichloropyridine), 1.72 g (21 mmol) of sodium acetate and 25 ml of methanol were initially introduced into an autoclave. Carbon monoxide was passed through the autoclave several times in order to replace the air with carbon monoxide. Carbon monoxide at 15 bar was then injected into the autoclave. The reaction mixture was heated to 135° C. (bath temperature) and stirred for one hour. After cooling to room temperature, the crude product was concentrated in vacuo (30 mbar) and chromatographed on silica gel 60 (eluent hexane/ethyl acetate 1:1). The product had a melting point of 120.8° to 122.5° C. The yield was 1.52 g (78 percent) of white powder. Other data concerning the product was:

MS; m/e: 195($M^+$), 165,137,105

$^1$H-NMR(CDCl$_3$): δ=

8.31(d, 2H);

8.02 (t, 1H);

4.02 (s, 6H).

EXAMPLE 2

Dimethyl 2,6-pyridinedicarboxylate

The procedure was as described in Example 1, but instead of methanol, the same volume of ethanol and, instead of 21 mmol, 57 mmol of sodium acetate were employed. After a reaction time of 1 hour at a bath temperature of 135° C., 1.96 g (88 percent) of white powder was obtained. The product had a melting point of 41.50 to 42.8° C. Other data concerning the product was:

MS; m/e: 224, 223($M^+$); 208; 179; 151; 123; 105

$^1$H-NMR(CDCl$_3$): δ=

8.28(d, 2H);

8.00(t, 1H);

4.50(q, 4H);
1.45(t, 6H).

EXAMPLE 3
Diethyl 2,6-pyridinedicarboxylate

The procedure was as described in Example 1, but instead of 25 ml of methanol, 25 ml of tetrahydrofuran and 30 ml of ethanol were employed. After a reaction time of 3 hours at a bath temperature of 150° C., 0.56 g (25.1 percent) of white powder was obtained.

EXAMPLE 4
Diethyl 2,6-pyridinedicarboxylate

The procedure was as described in Example 1, but instead of methanol, the same volume of ethanol and instead of 4.6 mg of palladium(II) acetate, 14.0 mg of bis(triphenylphosphine)palladium(I) chloride were employed. After a reaction time of 2 hours at a bath temperature of 175° C., 1.54 g (69 percent) of white powder were obtained.

EXAMPLE 5
Diethyl 2,6-pyridinedicarboxylate

The procedure was as described in Example 2, but instead of 166 mg of 1,1'-bis(diphenylphosphino)ferrocene, 128 mg of 1,4-bis(diphenylphosphino)butane was employed. After a reaction time of 3 hours at a bath temperature of 150° C., 1.64 g (73.5 percent) of white powder was obtained.

EXAMPLE 6
Dibutyl 2,6-pyridinedicarboxylate

The procedure was as described in Example 1, but instead of methanol, the same volume of butanol was employed. After a reaction time of 1 hour at a bath temperature of 135° C., 2.45 g (85 percent) of white powder was obtained. The product had a melting point of 65.5° to 65.9° C. Other data concerning the product was:

MS: m/e: 280 (M$^+$); 236; 224; 206; 179; 150; 123; 105; 78

$^1$H-NMR (CDCl$_3$): 67 =
8.28 (d, 2H);
7.98 (t, 1H);
5.32 (sept, 2H);
4.42 (t, 4H);
1.82 (quint, 4H);
1.50 (sext, 4H);
0.99 (t, 6H).

EXAMPLE 7
Dicyclohexyl 2,6-pyridinedicarboxylate

The procedure was as described in Example 1, but instead of methanol, the same volume of cyclohexanol was employed. After a reaction time of 1 hour at a bath temperature of 135° C., 1.7 g (51 percent) of white powder was obtained. The product had a melting point of 111.6° to 112.3° C. Other data concerning the product was:

MS: m/e: 331 (M$^+$); 287; 250; 219; 205; 168; 150; 123

$^1$H-NMR (CDCl$_3$): δ=
8.22 (d, 2H);
7.97 (t, 1H);
5.10 (sept, 2H);
2.1–1.3 (m, 22H).

EXAMPLE 8
Diethyl 3-chloro-2,6-pyridinedicarboxylate

The procedure was as described in Example 2, but instead of 1.48 g (10 mmol) of 2,6-dicholorpyridine, 1.82 g (10 mmol) of 2,3,6-trihloropyridine was employed. After a reaction time of 1 hour at a bath temperature of 135° C., 1.98 g (76 percent) of colorless oil was obtained. Other data concerning the product was:

MS: mle: 257 (M$^+$); 213; 185; 139; 113

$^1$H-NMR (CDCl$_3$): δ=
8.15 (d, 1H);
7.93 (d, 1H);
4.50 (q, 2H);
4.48 (d, 2H);
1.44 (t, 3H);
1.43 (t, 3H).

What is claimed is:

1. A process for the preparation of a 2,6-pyridinedicarboxylic acid ester of the formula:

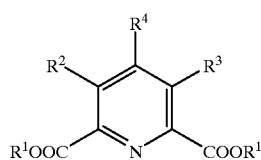

I wherein R$^1$ is a C$_{1-6}$-alkyl group, a C$_{3-8}$-cycloalkyl group, an aryl group or an arylalkyl group, and R$^2$ and R$^3$ independently of one another are hydrogen or chlorine and R$^4$ is hydrogen, a C$_{3-8}$-alkyl group, a C$_{1-8}$-alkyloxy group or fluorine, characterized in that a halopyridine of the formula:

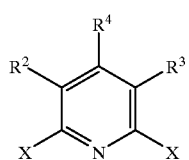

II wherein R$^2$, R$^3$ and R$^4$ have the above-mentioned meanings and X is a chlorine or bromine, is reacted with carbon monoxide and an alcohol of the formula:

III wherein R$^1$ has the above-mentioned meaning, in the presence of a base and of a complex of palladium, using a bisdiphenylphosphine of the formula:

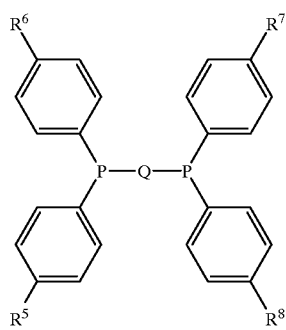

IV wherein Q is a C$_3$–C$_6$-alkanediyl group or a 1,1$^1$-ferrocenediyl group having cyclopentadienyl groups which are optionally substituted by C$_1$–C$_4$-alkyl or aryl groups and $R^5$ to $R^8$ independently of one another are hydrogen, $C_1$–$C_4$-alkyl, $C_1$–$C_4$-alkoxy, monofluoromethyl, difluoromethyl, trifluoromethyl, fluorine, aryl, aryloxy, cyano or dialkylamino, the base is an alkali metal or alkaline earth metal acetate, carbonate, hydrogen carbonate, phosphate or hydrogen phosphate, the reaction temperature is 100° to 250° C. and the carbon monoxide pressure is 1 to 200 bar.

2. The process according to claim 1, wherein $R^1$ is a methyl group, ethyl group, butyl group or cyclohexyl group.

3. The process according to claim 2, wherein palladium is employed in the form of bis(triphenylphosphine)palladium (II) chloride or palladium(II) acetate.

4. The process according to claim 3, wherein the bis-diphenylphosphine is 1,1'-bis(diphenylphosphine)ferrocene or 1,4-bis(diphenylphosphino)butane.

5. The process according to claim 1, wherein palladium is employed in the form of bis(triphenylphosphine)palladium (II)chloride or palladium(II)acetate.

6. The process according to claim 1, wherein the bis-diphenylphosphine is 1,1'-bis(diphenylphosphine)ferrocene or 1,4-bis(diphenylphosphino)butane.

7. The process according to claim 4, wherein the carbon monoxide pressure is 5 to 50 bar.

8. The process according to claim 7, wherein the reaction temperature is 140° to 195° C.

9. The process according to claim 8, wherein the reaction time is 1 to 20 hours.

10. The process according to claim 1, wherein the carbon monoxide pressure is 5 to 50 bar.

11. The process according to claim 1, wherein the reaction temperature is 140° to 195° C.

12. The process according to claim 1, wherein the reaction time is 1 to 20 hours.

13. The process of claim 1, wherein Q in formula IV is a straight-chain or branched alkanediyl group having 3 to 6 C atoms.

14. The process of claim 1, wherein Q in formula IV is a 1,1'-ferrocenediyl group, having cyclopentadienyl groups which are optionally substituted with $C_1$–$C_4$-alkyl or aryl groups.

* * * * *